United States Patent
Tang et al.

(10) Patent No.: US 12,005,183 B2
(45) Date of Patent: Jun. 11, 2024

(54) SYSTEMS AND METHODS FOR CONDUCTING SMOKE EVACUATION DURING LAPAROSCOPIC SURGICAL PROCEDURES

(71) Applicant: Conmed Corporation, Utica, NY (US)

(72) Inventors: Raymond Yue-Sing Tang, Rosemead, CA (US); Kenneth Blier, Cheshire, CT (US); Ralph Stearns, Bozrah, CT (US); Kurt Azarbarzin, Fairfield, CT (US); Dominick Mastri, Bridgeport, CT (US)

(73) Assignee: Conmed Corporation, Largo, FL (US)

( * ) Notice: Subject to any disclaimer, the term of this patent is extended or adjusted under 35 U.S.C. 154(b) by 533 days.

(21) Appl. No.: 16/851,448

(22) Filed: Apr. 17, 2020

(65) Prior Publication Data

US 2020/0238025 A1 Jul. 30, 2020

Related U.S. Application Data

(62) Division of application No. 14/907,517, filed as application No. PCT/US2013/070933 on Nov. 20, 2013, now abandoned.

(60) Provisional application No. 61/826,088, filed on May 22, 2013, provisional application No. 61/728,608, filed on Nov. 20, 2012.

(51) Int. Cl.
*A61M 13/00* (2006.01)
*A61B 17/34* (2006.01)

(52) U.S. Cl.
CPC ....... *A61M 13/006* (2014.02); *A61B 17/3462* (2013.01); *A61B 17/3474* (2013.01); *A61B 2218/006* (2013.01); *A61B 2218/008* (2013.01); *A61M 2205/3337* (2013.01);
(Continued)

(58) Field of Classification Search
CPC .. A61M 13/00; A61M 13/003; A61M 13/006; A61M 2205/3344; A61B 17/3474; A61B 2218/006; A61B 2218/008
See application file for complete search history.

(56) References Cited

U.S. PATENT DOCUMENTS

| 4,735,603 A | 4/1988 | Goodson et al. |
| 5,364,372 A | 11/1994 | Danks et al. |

(Continued)

FOREIGN PATENT DOCUMENTS

| CN | 102264310 A | 11/2011 |
| WO | 2010042204 A2 | 4/2010 |

OTHER PUBLICATIONS

Notification of First Office Action dated Apr. 29, 2016 in connection with CN Application No. 201380060681.4.
(Continued)

*Primary Examiner* — Kami A Bosworth
(74) *Attorney, Agent, or Firm* — Locke Lord LLP; Scott D. Wofsy

(57) ABSTRACT

An insufflation and smoke evacuation system for use during laparoscopic surgical procedures is disclosed that includes a pump for circulating pressurized gas within the system, a tri-lumen cannula communicating with an insufflation source by way of an insufflation supply line and with the supply side of the pump by way of a pressurized gas supply line, and a single lumen cannula communicating with a suction side of the pump by way of a vacuum line, wherein a communication line extends between the tri-lumen cannula and the vacuum line.

3 Claims, 4 Drawing Sheets

(52) U.S. Cl.
CPC ............... *A61M 2205/3344* (2013.01); *A61M 2205/7545* (2013.01); *F04C 2270/041* (2013.01)

(56) References Cited

U.S. PATENT DOCUMENTS

| | | |
|---|---|---|
| 5,779,662 A | 7/1998 | Berman |
| 6,544,210 B1 | 4/2003 | Trudel et al. |
| 6,592,543 B1 | 7/2003 | Wortrich et al. |
| 7,285,112 B2 | 10/2007 | Stubbs et al. |
| 7,413,559 B2 | 8/2008 | Stubbs et al. |
| 2005/0107767 A1* | 5/2005 | Ott ....................... A61M 31/00 604/500 |
| 2007/0088274 A1 | 4/2007 | Stubbs et al. |
| 2007/0088275 A1 | 4/2007 | Stearns et al. |
| 2007/0088276 A1 | 4/2007 | Stubbs et al. |
| 2009/0137943 A1 | 5/2009 | Stearns et al. |
| 2010/0185139 A1 | 7/2010 | Stearns et al. |
| 2012/0130178 A1 | 5/2012 | Hartoumbekis et al. |

OTHER PUBLICATIONS

Extended Search Report dated May 12, 2016 in connectin with EP Application No. 13856218.6.

\* cited by examiner

SYSTEMS AND METHODS FOR CONDUCTING SMOKE EVACUATION DURING LAPAROSCOPIC SURGICAL PROCEDURES

CROSS-REFERENCE TO RELATED APPLICATIONS

This Application is a Divisional of U.S. patent application Ser. No. 14/907,517 filed on Jan. 25, 2016, which is a 371 U.S. National Phase Application of International Patent Application No. PCT/US2013/070933, filed Nov. 20, 2013, which application claims priority to U.S. Provisional Patent Application No. 61/826,088 filed May 22, 2013 and to U.S. Provisional Patent Application No. 61/728,608 filed Nov. 20, 2012, the entire contents of which are hereby incorporated by reference in their entireties.

BACKGROUND OF THE INVENTION

1. Field of the Invention

The subject invention is directed to laparoscopic surgery, and more particularly, to systems and methods for conducting smoke removal and evacuation from the abdominal cavity of a patient during a laparoscopic surgical procedure utilizing a dual lumen cannula.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device, e.g., a cannula or trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art.

Additionally, SurgiQuest, Inc., Milford, Conn. USA has developed surgical access devices that permit access to an insufflated surgical cavity without conventional mechanical seals, and has developed related systems for providing sufficient pressure and flow rates to such access devices, as described in whole or in part in U.S. Pat. No. 7,854,724.

While the systems and methods described above have generally been considered satisfactory for their intended purpose, there is an ongoing need for improved functionality in insufflation systems and related techniques.

SUMMARY OF THE INVENTION

The subject disclosure is directed to a new and useful surgical gas delivery system for use during laparoscopic surgical procedures, e.g., in an abdominal cavity of a patient, and more particularly, to an insufflation and smoke evacuation system that includes a pump for circulating pressurized gas within the system and a dual lumen cannula configured to provide access to the abdominal cavity of a patient, which includes a first lumen communicating with the source of insufflation fluid and a second lumen communicating with the pump.

In one embodiment of the subject invention, the dual lumen cannula includes a first lumen communicating with the source of insufflation fluid and a pressure side of the pump for delivering pressurized gas and insufflation fluid to the abdominal cavity, and a second lumen communicating with a suction side of the pump for removing gas from the abdominal cavity.

In another embodiment of the subject invention, the dual lumen cannula includes a first lumen communicating with the source of insufflation fluid and a second lumen communicating with a pressure side of the pump for delivering pressurized gas to the abdominal cavity. In addition, the system includes a second cannula which has a single lumen communicating with a suction side of the pump for removing gas from the abdominal cavity.

In certain embodiments of the subject invention, a bypass valve is operatively associated with the pump for controlling a gas circulation rate within the system. In addition, a mechanical seal is operatively associated with the second lumen to maintain abdominal pressure, and the first lumen serves as a sense line for sensing abdominal pressure. A filter device is also provided for filtering gas circulating through the system to remove smoke and debris therefrom.

These and other features of the system of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the subject invention without undue experimentation, preferred embodiments thereof will be described in detail herein below with reference to certain figures, wherein.

DETAILED DESCRIPTION OF PREFERRED EMBODIMENTS

Figure 1:
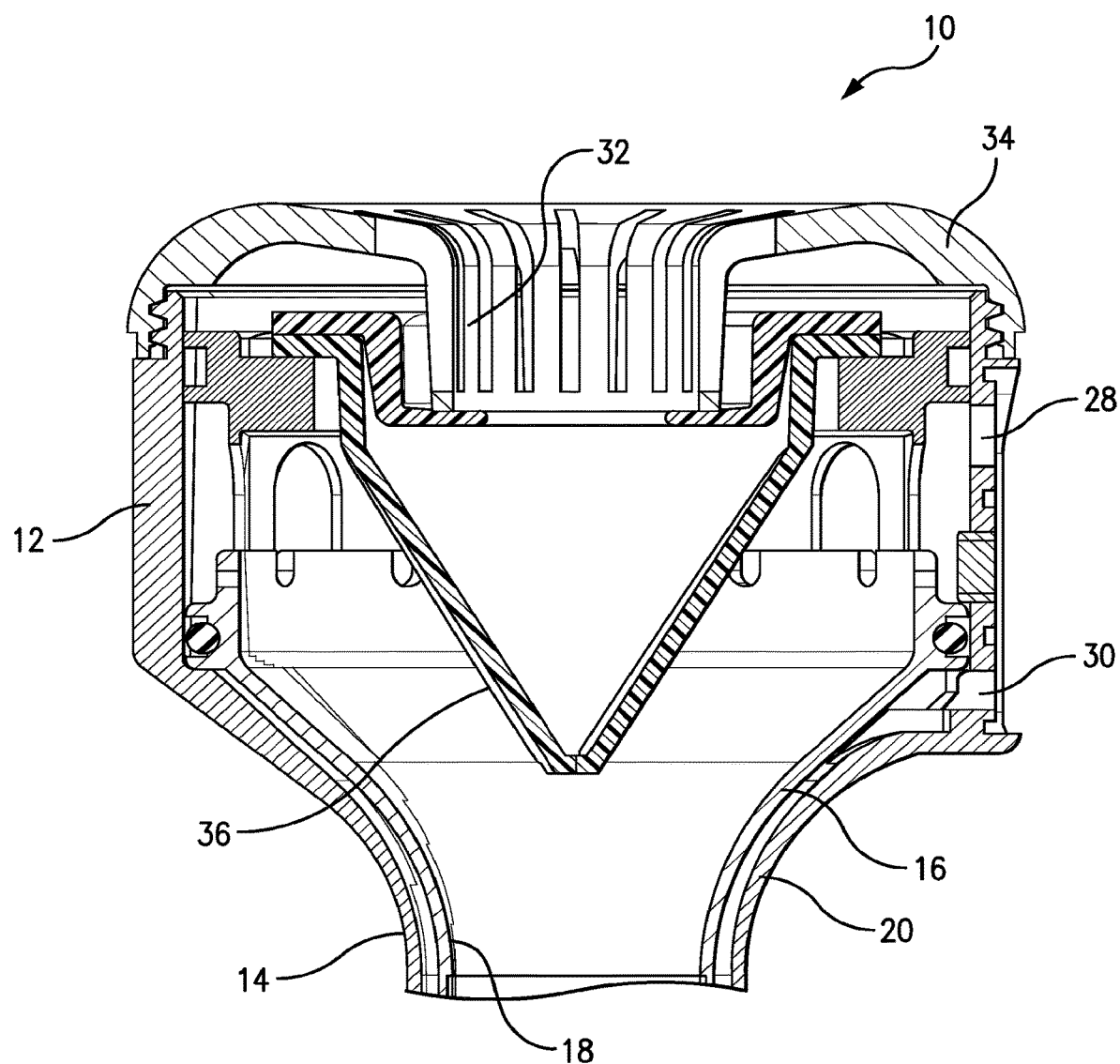
FIG. 1 is cross-sectional view of the upper portion of a dual lumen cannula constructed in accordance with a preferred embodiment of the subject invention, which includes, among other things a mechanical duckbill seal.

Reference will now be made to the drawings wherein like reference numerals identify similar structural features or aspects of the subject disclosure. For purposes of explanation and illustration, and not limitation, a partial view of an exemplary embodiment of an insufflation and smoke evacuation system in accordance with the disclosure is shown in FIG. 1 and is designated generally by reference character 10. Other embodiments of insufflation and smoke evacuation systems in accordance with the disclosure, or aspects thereof, are provided in FIGS. 2-4, as will be described. It is to be appreciated that the systems, devices and methods presented herein may be used for surgical gas delivery, including insufflation, smoke evacuation, and/or recirculation in connection with suitable surgical devices, and in applicable surgical procedures.

The present invention relates to multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids, such as with the above-mentioned surgical access devices described for example in U.S. Pat. No. 7,854,724; as well as those in U.S. Pat. Nos. 7,182,752; 7,285,112; 7,413,559 or 7,338,473; each of which is incorporated by reference herein in its entirety.

Use of a single multimodal system such as those described herein reduces costs by requiring purchase of only one system while achieving multiple functions, and also thereby reduces the amount of equipment needed in an operating room, thus reducing clutter and allowing space for other necessary equipment.

The present invention is particularly suited for minimizing the amount of equipment needed in a surgical operating room, in that the subject systems are capable of performing multiple functions, and therefore also allow flexibility of surgical technique. It is envisioned that the gas delivery system disclosed herein can be used in general laparoscopic procedures including but not limited to laparoscopic cholecystectomy, laparoscopic appendectomy, laparoscopic hernia repair, Nissen-Y and Lap Nephrectomy.

Those skilled in the art will readily appreciate that systems described in U.S. Pat. No. 7,854,724, for example, provide pressurized gas to and remove depressurized gas from specialized surgical access devices, which penetrate into a surgical cavity, such as a patient's abdominal cavity. These access devices are adapted and configured to form a pressure bather to inhibit the loss of insufflation gas to the atmosphere.

An example of an access device constructed in accordance with a preferred embodiment of the subject invention is illustrated in FIG. 1 and is designated generally by reference numeral 10. Access device 10 is configured as a dual lumen cannula. That is, it includes a proximal housing 12, an outer cannula 14 and an inner cannula 16. The inner cannula 16 defines a central or inner lumen 18 and an annular or outer lumen 20 is formed between the outer cannula 14 and the inner cannula 16.

The housing 12 includes a first flow port 28 communicating with the central lumen of the inner cannula 16 and a second flow port 30 communicating with the annular passage 20. A main access port 32 is provided in the end cap 34 of the housing 12, and a duckbill seal 36 is supported within the housing 12 to prevent the egress of pressurized gas from the device through the access port 32.

As discussed in more detail below with reference to FIG. 2, during use gas from the abdomen, e.g., pneumoperitoneum 116, interchanges with gas coming from the access device 10, a portion of which is collected and recycled through the system, and is re-pressurized along the way, passing through one or more filters, e.g., filter 123 described below. During this recycling process, smoke and/or other circulating debris, such as atomized fluids, are removed by the filters, improving visibility within the surgical cavity, thus aiding in the surgical procedure. An example of a filter that can be utilized with the subject invention is disclosed in U.S. Pat. No. 8,088,189, the disclosure of which is herein incorporated by reference in its entirety.

Figure 2:
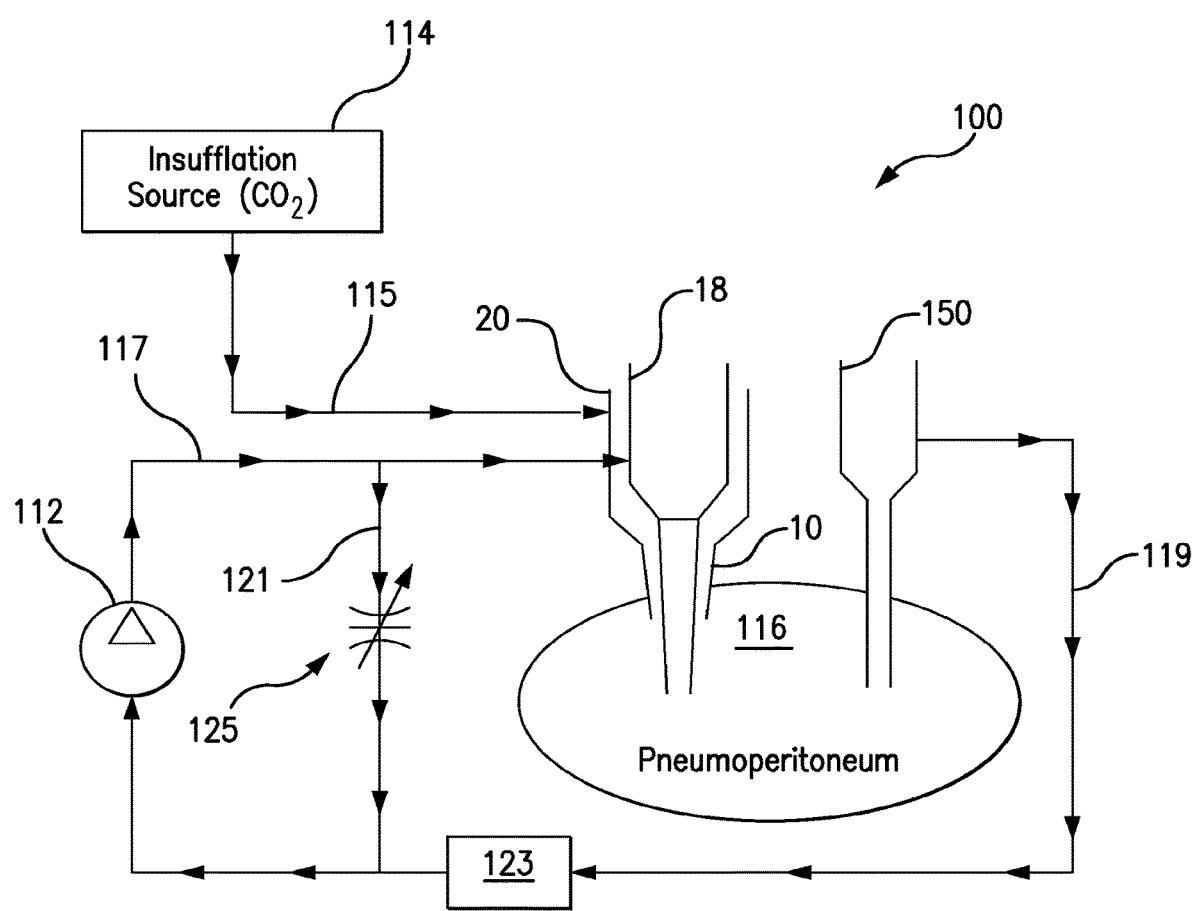
FIG. 2 is a schematic drawing of an embodiment of the insufflation and smoke evacuation system of the subject invention, which employs the dual lumen cannula shown in FIG. 1, as well as an additional single lumen cannula.

Referring now to FIG. 2, there is illustrated an insufflation and smoke evacuation system constructed in accordance with the subject invention and designated generally by reference numeral 100 that includes a recirculation pump 112 for circulating pressurized gas within the system. The system 100 includes a dual lumen cannula 10 as illustrated in FIG. 1. In this embodiment of the invention, the dual lumen cannula 10 includes a first or outer lumen 20 communicating with a source of insufflation fluid 114 through a conduit 115 connected to the flow port 30 in housing 12. The source of insufflation fluid 114 maintains pressure within pneumoperitoneum 116. The outer lumen 20 of dual lumen cannula 10 also serves as a sense line for sensing and controlling abdominal pressure within the system 100.

The dual lumen cannula 10 of system 100 further includes a second or central lumen 18 communicating with a pressure or supply side of the recirculation pump 112 through a conduit 117 connected to the flow port 28 in housing 12 for delivering pressurized gas to the abdominal cavity, e.g., for recirculation as described below.

In addition, the system 100 includes a second cannula 150 which has a single lumen that communicates with a suction side of the recirculation pump 112 through a conduit 119, e.g., by way of a luer connection, for removing gas from the abdominal cavity. System 100 further includes a bypass valve 125 that is operatively associated with the recirculation pump 112 through a conduit 121 connecting conduit 117 to conduit 119 to control the gas circulation rate within the system 100. When bypass valve 125 is closed, pump 112 recirculates gas through connecting conduit 117, central lumen 18, pneumoperitoneum 116, second cannula 150, and conduit 119, which includes a filter 123. Filter 123 can remove smoke, particles, moisture, and the like from the insufflation gas circulating through pneumoperitoneum 116. Bypass valve 112 can be opened and adjusted as needed to reduce the flow of recirculation through pneumoperitoneum 116.

Figure 3:
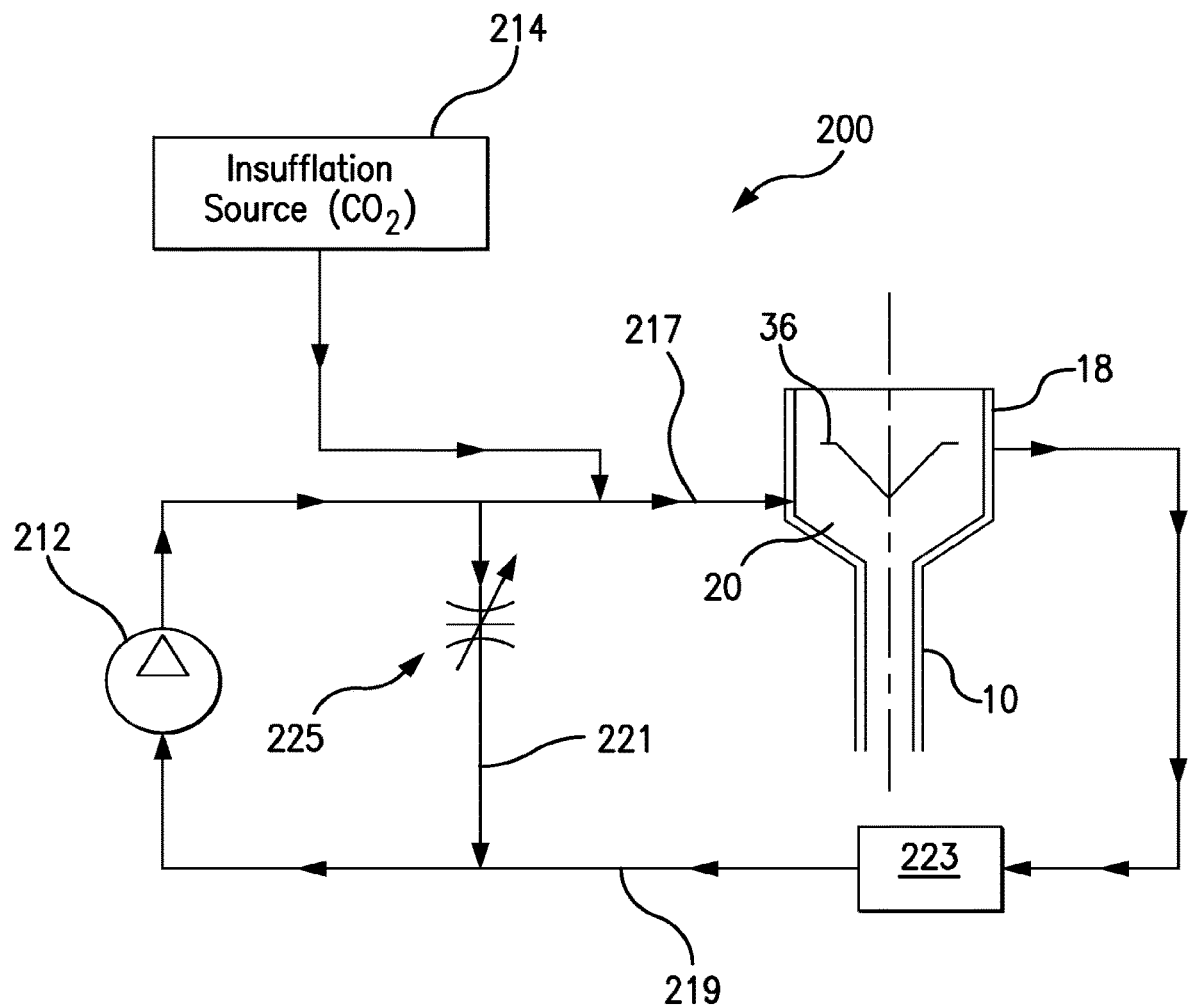
FIG. 3 is s schematic drawing of an embodiment of the insufflation and smoke evacuation system of the subject invention, which employs the dual lumen cannula shown in FIG. 1.

Referring now to FIG. 3, there is illustrated another insufflation and smoke evacuation system constructed in accordance with the subject invention and designated generally by reference numeral 200 that includes a recirculation pump 212 for circulating pressurized gas within the system. The system 200 further includes a dual lumen cannula 10 as illustrated in FIG. 1.

In this embodiment of the invention, the dual lumen cannula 10 includes a first annular lumen 20 communicating with a source of insufflation fluid 214 and a high pressure side (or supply side) of the pump 212 through a conduit 217 connected to the flow port 30 in housing 12. The annular lumen 20 of dual lumen cannula 10 also serves as a sense line for sensing abdominal pressure within the system 200.

In system 200, the dual lumen cannula 10 further includes a second lumen 18 communicating with the suction side of the recirculation pump 212 through a conduit 219 connected to the flow port 28 of housing 12 for removing gas from the abdominal cavity, e.g. pneumoperitoneum 116 of FIG. 1. In this embodiment, second lumen 18 has only one line, namely conduit 219, which is a suction line, i.e., there is no sense/insufflation line for second lumen 18. System 200 further includes a bypass valve 225 that is operatively associated with the recirculation pump 212 through a conduit 221 connecting conduit 217 to conduit 219 to control the rate of gas circulation within the system 200. Bypass valve 225 can be used to control the amount of recirculation flow through dual lumen cannula 10 as described above. Filter 223 operates as described above with respect to filter 123.

Figure 4:
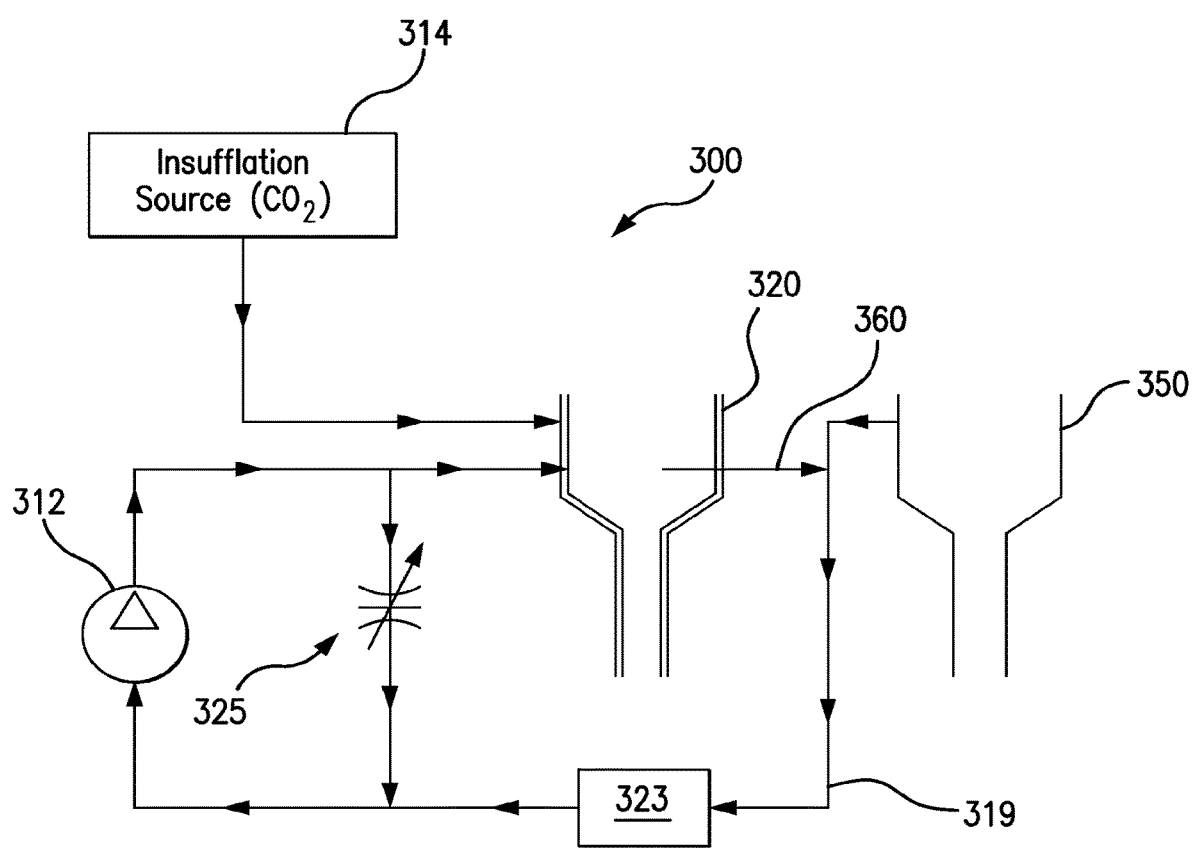
FIG. 4 is a schematic drawing of yet another embodiment of the insufflation and smoke evacuation system of the subject invention, which employs a tri-lumen cannula, as well as an additional single lumen cannula.

Referring to FIG. 4, there is there is illustrated yet another insufflation and smoke evacuation system designated generally by reference numeral 300. System 300 includes a source of insufflation gas 314, pump 312, bypass valve 325, second cannula 350, and filter 323, and is substantially identical to the system 100 shown in FIG. 2, except that system 300 includes a tri-lumen cannula 320 and a communication line 360 that extends between the inner bowl area of the cannula 320 and the vacuum line 319. As a result, if the tri-lumen cannula 320 is used as an access port for a laparoscope, smoke will exit the abdominal cavity in an area that is located away from the distal end of the scope so as not to adversely impact visibility through the scope.

While shown and described in the exemplary context of insufflation of a peritoneum space, those skilled in the art will readily appreciate that any suitable space can be insufflated with the systems and methods described herein without departing from the scope of this disclosure.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. An insufflation and smoke evacuation system for use during laparoscopic surgical procedures, comprising:
    a) an insufflation source;
    b) a pump for circulating pressurized gas within the system, the pump having a supply side and a suction side;
    c) a tri-lumen cannula having a proximal housing defining an inner bowl area and a longitudinal conduit extending distally from an exit at a distal end of the proximal housing, the proximal housing communicating with the insufflation source by way of an insufflation gas supply line and with the supply side of the pump by way of a pressurized gas supply line; and
    d) a single lumen cannula communicating with the suction side of the pump by way of a vacuum line, wherein a communication line extends between the inner bowl area of the tri-lumen cannula and the vacuum line, such that the proximal housing of the tri-lumen cannula has a first gas inflow path, a second gas inflow path, and a gas outflow path, wherein the first gas inflow path is associated with the insufflation gas supply line, the second gas inflow path is associated with the pressurized gas supply line and the gas outflow path is associated with the communication line that extends between the inner bowl area of the tri-lumen cannula and the vacuum line, wherein the gas outflow path extends radially from the proximal housing and is separate and distinct from the exit at the distal end of the proximal housing, and wherein the longitudinal conduit of the tri-lumen cannula is configured to be used as an access port for a laparoscope during laparoscopic surgical procedures, and the tri-lumen cannula and the single lumen cannula are configured to be arranged within an abdominal cavity such that when smoke is generated within the abdominal cavity during a laparoscopic surgical procedure, the smoke will exit the abdominal cavity through the single lumen cannula in an area located away from a distal end of the laparoscope so as not to impact visibility through the laparoscope.

2. An insufflation and smoke evacuation system as recited in claim 1, further comprising a bypass valve in parallel communication with the pump.

3. An insufflation and smoke evacuation system as recited in claim 1, further comprising a filter device operatively associated with the vacuum line.

* * * * *